United States Patent
Victor (10) Patent No.: US 6,974,414 B2
(45) Date of Patent: Dec. 13, 2005

(54) SYSTEM AND METHOD FOR MONITORING AND MANAGING DRIVER ATTENTION LOADS

(75) Inventor: Trent Victor, Göteborg (SE)

(73) Assignee: Volvo Technology Corporation, Göteborg (SE)

(*) Notice: Subject to any disclaimer, the term of this patent is extended or adjusted under 35 U.S.C. 154(b) by 0 days.

(21) Appl. No.: 10/248,798

(22) Filed: Feb. 19, 2003

(65) Prior Publication Data

US 2003/0181822 A1 Sep. 25, 2003

Related U.S. Application Data

(60) Provisional application No. 60/357,135, filed on Feb. 19, 2002, and provisional application No. 60/418,171, filed on Oct. 15, 2002.

(51) Int. Cl.[7] .................................................. A61B 5/00
(52) U.S. Cl. ...................... 600/300; 125/898; 340/576
(58) Field of Search ............................ 600/300–301, 600/558; 340/574–576; 180/272, 220, 446; 701/1, 96; 128/898

(56) References Cited

U.S. PATENT DOCUMENTS

| | | | |
|---|---|---|---|
| 5,585,785 A | | 12/1996 | Gwin et al. |
| 5,786,765 A | * | 7/1998 | Kumakura et al. ......... 340/576 |
| 5,900,819 A | | 5/1999 | Kyrtsos |
| 6,130,617 A | * | 10/2000 | Yeo ............................ 340/575 |
| 6,599,243 B2 | * | 7/2003 | Woltermann et al. ....... 600/300 |

OTHER PUBLICATIONS

M. Hoedemaeker, S.N. de Ridder, W. H. Janssen, *Review of European Human Factors Research on Adaptive Interface Technologies for Automobiles*, May 14, 2002, pp. 1–60, TNO Human Factors, TNO Report, TM–02–C031, Netherlands Organisation for Applied Scientific Research, SOESTERBERG, Netherlands.

TNO Human Factors, TNO Report, TM–02–C031, 2002, M. Hoedemacker, et al, *Review of European Human Factors Research on Adaptive Interface Technologies for Automobiles*.

Human Interface Lab, Paper, 2002, C, Wood, et al, *Driver Advocate™ Tool*.

Delphi Automotive Systems, Delphi Technology Paper 01/13, *Integrated Safety Systems*.

IEEE Spectrum, Critical Challenges 2002, Jan. 2002, W. D. Jones, *Building Safer Cars*.

European AutomotiveDesign, Feb. 2001, *Drivers on the Blink*.

Society of Automotive Engineers, Inc., 2000–01–C075, 2000, D. Remboski, et al, *Driver Performance Improvement through the Driver Advocate: A Research Initiative toward Automotive Safety*.

* cited by examiner

*Primary Examiner*—Max F. Hindenburg
*Assistant Examiner*—Michael C. Astorino
(74) *Attorney, Agent, or Firm*—Novak Druce & Quigg, LLP (57) ABSTRACT

System and method for monitoring the physiological behavior of a driver that includes measuring a physiological variable of a driver, assessing a driver's behavioral parameter on the basis of at least said measured physiological variable, and informing the driver of the assessed driver's behavioral parameter. The measurement of the physiological variable can include measuring a driver's eye movement, measuring a driver's eye-gaze direction, measuring a driver's eye-closure amount, measuring a driver's blinking movement, measuring a driver's head movement, measuring a driver's head position, measuring a driver's head orientation, measuring driver's movable facial features, and measuring a driver's facial temperature image.

65 Claims, 10 Drawing Sheets

SYSTEM AND METHOD FOR MONITORING AND MANAGING DRIVER ATTENTION LOADS

CROSS REFERENCE TO RELATED APPLICATIONS

The present patent application claims the benefit of U.S. Provisional Patent Application Nos. 60/357,135 filed 19 Feb. 2002 and 60/418,171 filed 15 Oct. 2002. Said applications are expressly incorporated herein by reference in their entireties.

BACKGROUND OF INVENTION

1. Field of the Invention(s)

The present invention(s) relate to systems and methods that facilitate driver safety; and more particularly, to remedies against the effects of drowsiness, distraction and similar compromising conditions to a driver's driving capabilities.

2. Background of the Invention(s)

Drivers of all types of vehicles are often unaware of the effects that drowsiness and distraction have on their own abilities for vehicle control. Humans in general, and particularly as drivers, are poor judges of their own performance capabilities. Typically, a driver's self-impression of his or her capabilities is better than actuality. Even persons who have basically good driving skills, will not perform uniformly at all times when behind the wheel of a vehicle. Furthermore, there are many times during driving trips that very little demand is placed on the driver with respect to execution of driving tasks. As a result, drivers are lulled into states of mind where little attention is being devoted to the driving task. Not surprisingly, driver inattention is a leading cause of vehicular collisions, and especially automotive collisions. According to a Nation Highway and Transportation Safety Administration (NHTSA) study of over two and one-half million tow-away crashes in a year's time, driver inattention is a primary cause of collisions that accounts for an estimated twenty-five to fifty-six percent of crashes. In that study, inattention was defined as having three components: visual distraction, mental distraction (looking without seeing) and drowsiness. Common crash types caused by inattention are: rear-end collisions, collisions at intersection, collisions while lane changing or merging, road departures, single vehicle crashes, and crashes that occur on low speed limit roadways.

Drowsy drivers are a well known phenomenon. At least one survey has indicated that fifty-seven percent of drivers polled had driven while drowsy in the previous year, and twenty-three percent had actually fallen asleep at the wheel. It is known that fatigue impairs driver performance, alertness and judgment. Collisions caused by drowsiness are a serious road safety problem, and fatigue has been estimated to be involved in as many as twenty-three percent of all crashes.

From a technological perspective, there is an ongoing and rapid increase of new information systems and functionalities that may be used within vehicles including mobile telephones, navigation aids, the internet, and other types of electronic services. The effect of mobile telephone use on drivers has been foremost in the public eye because of their widespread use, but sales of navigation aids and IT services are also growing fast. Mobile telephones alone have been estimated to have caused 300–1000 fatalities in one years time in the United States, and this is projected to reach 4000 fatalities per year in 2004. Distractions such as handheld telephone use, sign reading, eating food, interaction with other passengers, observing objects and manipulating devices in-the vehicle have the potential for capturing a driver's attention in an excessive way and thus also compromising safety. It is especially important that driving safety not be compromised as these new types of services and activities become more common place in the driving environment.

Driver workload increases based on utilization of these new functionalities and technologies. In this context, "workload" should be understood to refer to how busy a person is and the amount of effort they need to perform required tasks. When a driver has many things to do and is experiencing high workload, a high attention demand is being made on the driver in that there is much to be done at the same time. Drivers often attend to things that are not related to driver control of the vehicle and are therefore technically irrelevant to the driving situation. These things are often called secondary tasks and are potential distracters from driver attention to primary driving tasks. A secondary task becomes a distraction (including visual-, auditory-, cognitive-, and biomechanical distractions) when the driver's attention is captured thereby to a degree that insufficient attention is left for the primary control tasks of driving. As a result, driving performance such as lane keeping and speed control are compromised as ultimately is safety.

Figure 1:
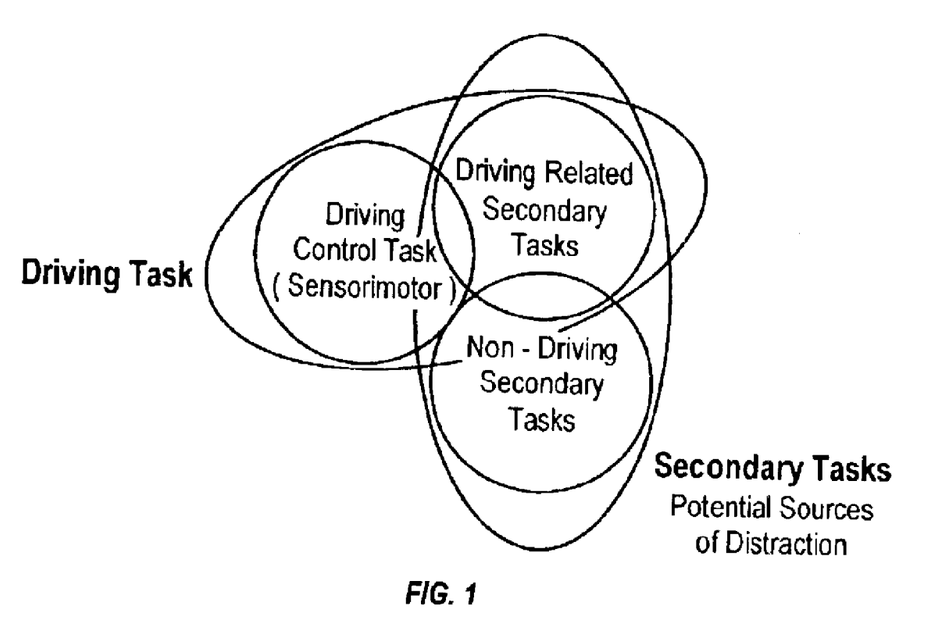
FIG. 1 is a diagrammatical representation of the inter-relationship of driving control tasks and secondary tasks.

Driving tasks and secondary tasks overlap in the sense that some secondary tasks are driving related as diagrammatically shown in FIG. 1. Two difficulties arise from this relationship between the driving and secondary tasks. First, it can be difficult to delineate which secondary task information is "irrelevant to the driving situation" and which is not; and second, certain driving related secondary tasks, for instance, looking for a street sign or planning a driving route may also compromise safety as graphically depicted in FIG. 1.

It should also be appreciated that the driver is often unaware of the effects of distraction on the driving task. Also, drivers cannot reliably determine when they are impaired by fatigue to the point of having a serious vigilance lapse or uncontrolled sleep attacks. The attention management systems outlined herein are intended to increase safety by assisting the driver in drowsy, distractive, and/or high workload situations.

SUMMARY OF INVENTION

The attention management systems and methods disclosed herein have as an objective to increase safety by assisting drivers in drowsy, distractive, and/or high workload situations. Functional specifications are provided for a number of attention management systems that can be characterized to include drowsiness managers, distraction managers, managers for distraction adaptation of forward collision and lane change warning systems, and workload managers that are at least in part controlled based on driving demand estimations observed or deduced from visual behavior of the driver. A hardware system that can be suitably employed to perform these driver attention management tasks is also described. A "platform" for development of the instant drowsiness and distraction manager based on Human Machine Interaction (HMI) is also disclosed, as is description of continuous and post-trip attention feedback systems. The HMI approach has as an objective thereof to counteract driver inattention by providing both imminent collision warnings, as well as attention-feedback to cause positive behavioral change.

DETAILED DESCRIPTION

In at least one embodiment, the present invention provides a system and method that enables the implementation of attention management concepts in a vehicle, including exemplary hardware upon which the inventive functionalities can be accomplished. Several basic questions and goals are addressed herein, including: what visually derived support do drivers need and how should it be conceptualized to achieve acceptance; how can real-time recognition of driver visual behavior be applied to reduce driving errors and prevent accidents; what is the commercial feasibility of implementation. Functional descriptions are provided for exemplary drowsiness managers; distraction managers, distraction adaptation of forward collision and lane change warning systems; and workload managers. Systems and methods for implementing driving demand estimation from visual behavior are also included.

One or more of these systems and methods are individually, as well as collectively, described as making-up a so-called attention management system. One possible component of these systems, as well as a component of the several inventions described herein, is the attention support demonstrator that can be used to implement these systems and methods for demonstration and testing. Examples of driving demand estimation from visual behavior are also described herein.

Figure 2:
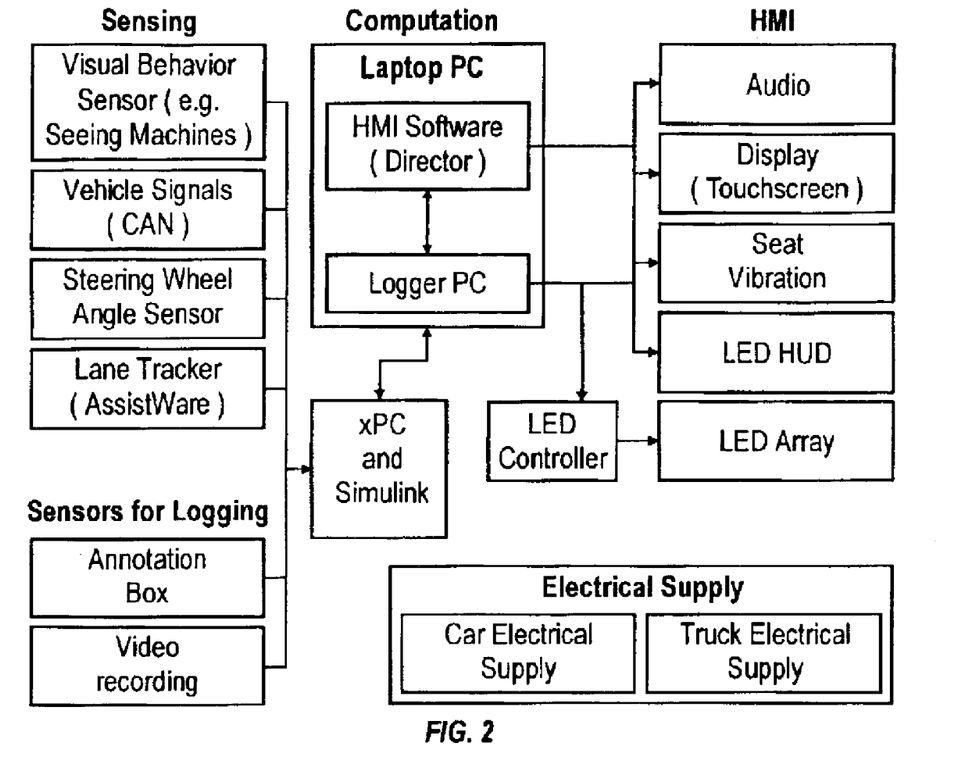
FIG. 2 is a flowchart representing one embodiment of an attention management system that includes hardware and functional modules for sensing, computation, HMI, and electrical supply.

In one embodiment, the attention management system includes hardware for (1) sensing, (2) computation, (3) HMI, and (4) electrical supply. The units or functional modules can be exemplarily configured (interrelated) as illustrated in FIG. 2, and are suitable for implementation in such vehicles as automobiles and trucks.

A visual behavior sensor is employed such as that which is available from the company, SeeingMachines, and which can be adapted to be installed in a vehicle. This type of system can include (1) a stereo camera head, (2) a personal computer (PC), and (3) appropriate driving software. A visual behavior sensor such as that produced and sold under the trade name SMARTEYE may also be optionally employed.

Vehicle performance signals can be acquired from the CAN bus. A steering wheel angle sensor can also utilized, as well as lane tracking hardware and software. An annotation box and video recording hardware is utilized. An onboard personal computer, or similarly capable computing device is utilized. Alternatively, and especially to facilitate testing and implementation, a laptop computer can be employed that exemplarily runs such software as "Director" and "Simulink." An xPC can also be installed and utilized. From a hardware perspective, LED controller hardware is employed. Audio HMI (warning sounds, recorded messages) are provided for via the computing device. A touch-screen for user input can also be utilized. It should be appreciated that some of these embodiments are suitable for product development and facilitate system testing, but when commercialized, the several components are integrated directly into the vehicle.

A seat vibration arrangement or similar driver alert can be included. In a preferred embodiment, a LED HUD (heads up display) is employed. A LED array (display), controlled by a LED controller can also be utilized. An electrical supply for the entire system can be tapped from the carrying vehicle.

A drowsiness manager can be implemented in two configurations. In a first example, it is entirely PC based; that is, no external hardware or external communication capabilities are required. This embodiment is scenario based; that is, tracking of a drowsiness episode based on real PERCLOS (analysis that considers scan patterns, number and length of fixations, saccade latency and the like) data rather than in real-time. The hardware functionality stimulates the driver via such stimuli as a visual display such as LED-based or HUD, or physical stimulation such as seat vibration. In another embodiment, HMI hardware and Simulink communication is implemented.

A "platform" upon which several drowsiness manager countermeasures may be implemented is desirable, and upon which tests may be conducted. An exemplary platform for such implementation is schematically illustrated in FIG. 3.

Figure 3:
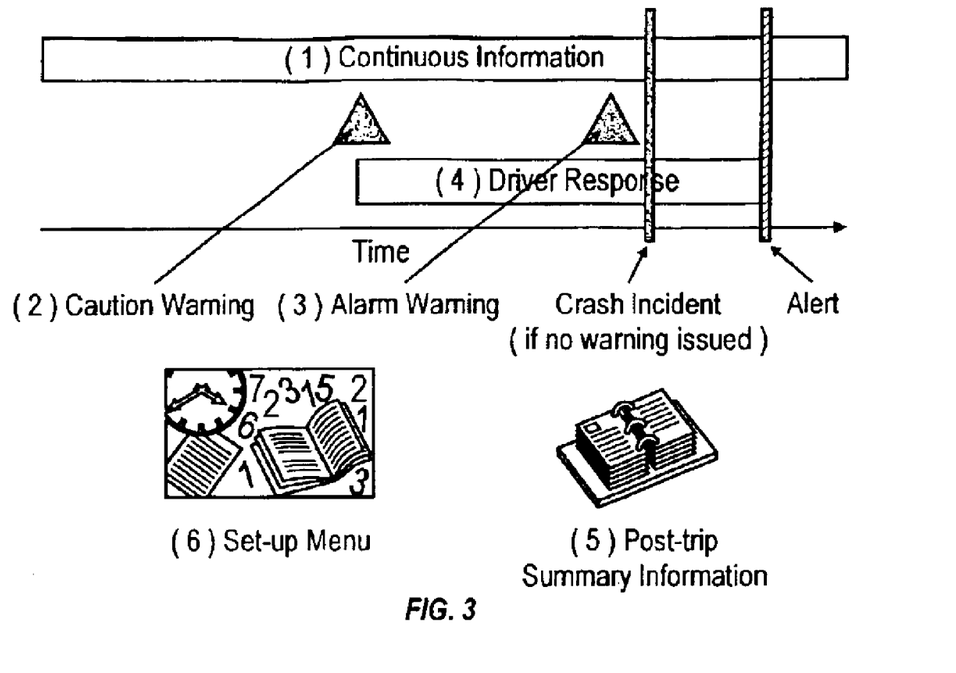
FIG. 3 is a diagrammatical representation of a platform upon which several drowsiness manager countermeasures may be exemplarily implemented.
Figure 4A:
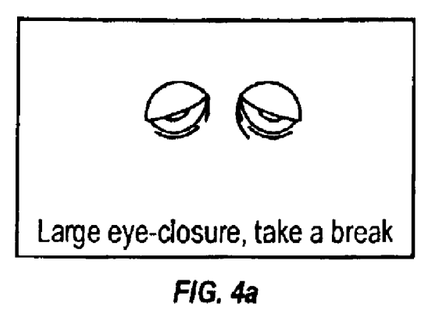
FIG. 4 depicts exemplary representations of possible display warnings to a driver.
Figure 4B:
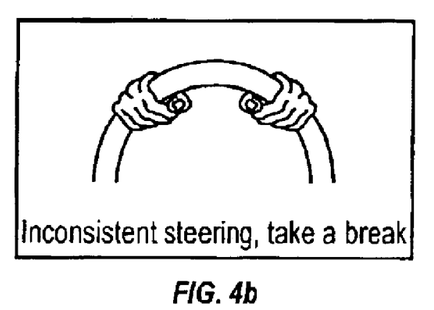
Figure 4C:
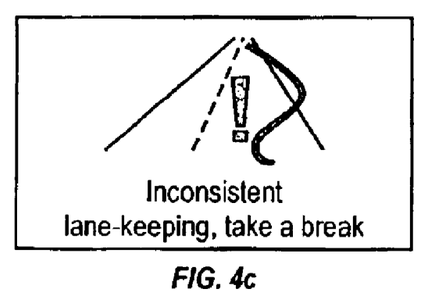
Figure 4D:
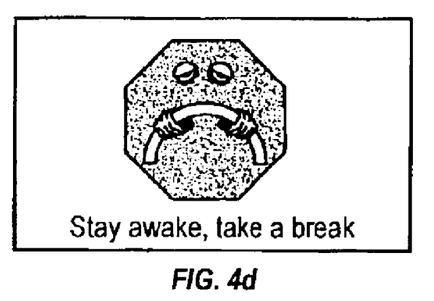

The illustration of FIG. 3 may be considered to depict a director program. Such an arrangement is easy to change with respect to different HMI components; for instance, to provide (1) continuous information streaming to the driver, to provide (2) cautionary warnings, (3) eminent danger warning alarms, (4) driver response tests, (5) post trip summary information, and (6) operator input set-up menu (s).

In one embodiment of the invention, a caution warning to the driver is provided. The driver is able to choose between warning versions, but is not able to completely disable the warning. Exemplarily, a beep followed by an optional voice message warning can be played to the driver such as "<automated insertion of drowsiness cause>, 'take a break.'" An icon can be alternatively displayed to the driver either individually, in conjunction with an audible warning, or together with a printed version of the warning.

Exemplary icon warnings are shown in FIGS. 4(a)–(d) for (a) large eye closure detection, (b) inconsistent steering detection, (c) inconsistent lane-keeping detection, and (d) driver drowsiness detection. One or more of these icons can be simultaneously displayed depending upon detected driver conditions.

In another embodiment, a microphone is included so that the driver can record or supply his or her own warning much like in a telephone answering machine and other customizable audio play-back devices.

In still another embodiment, driver physical-stimulation warnings are applied. Preferably, the driver can choose between warning-types in the set-up menu, but in at least one embodiment the operator is prevented from completely disabling the physical warning. An example of such a physical stimulation would be seat vibration.

In another version, a flashing "HUD" LEDs may be used to sharply stimulate the driver; again, alone or in conjunction with the other types of warnings described herein. In a preferred embodiment, capabilities are provided to the driver for enabling up to three of the described warning types to be simultaneous presented when active.

A driver response functionality; that is, reaction-time to a signal, is also provided. With regard to this functionality, the driver is able to both enable and disable, as well as choose between warning versions in the set-up menu.

Figure 5:
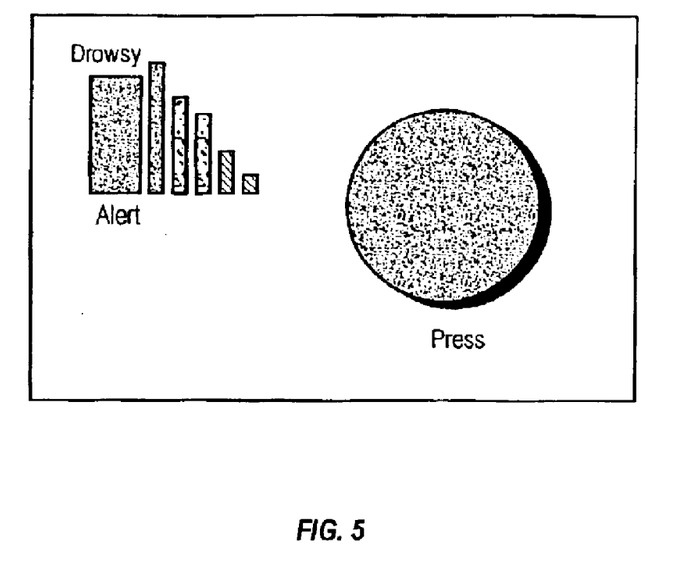
FIG. 5 depicts an exemplary, interactive, driver response panel.

In a predetermined amount of time, for example five to eight seconds post-warning, a driver response function operates. Exemplarily, there will be a beep, with text "Press" under a button presented on a touch screen as illustrated in FIG. 5. If the driver does not react within the prescribed amount of time, or according to some other reaction time based algorithm, then an alarm warning will issue. This continues until the driver stops the vehicle, becomes alert and this fact is system-detected, or the driver turns the function off.

In order to provide customizing capabilities to the operator, exemplary options that may be selected via the HMI components are illustrated below:

| HMI Component | Option(s) |
| --- | --- |
| (1) Continuous drowsiness feedback | Continuous feedback on/off Choice of one of several versions |
| (2) Caution Warning | Voice message on/off Default message on/off User supplied message on/off Use multiple icons or Use default icon |
| (3) Alarm/ Stimulation Warning | Choice of following (at least one must be checked) Seat |

-continued

| HMI Component | Option(s) |
| --- | --- |
| | vibration on/off Sound on/off HUD visual warning on/off Fan (not implemented in iteration 1) Scent (not implemented in iteration 1) Cut gas (not implemented in iteration 1) Drive to roadside (not implemented in iteration 1) Use multiple icons or Use default icon |
| (4) Driver Response | Driver response on/off |

A distraction manager can be exemplarily implemented in two embodiments. In a first embodiment, the distraction manager is entirely PC based with no external hardware or communication capabilities. It is scenario based; that is, a timeline of a distraction episode is given rather than in real-time. The hardware functionality is simulated. A second embodiment is based on a hardware implementation that includes the capability of real time communication.

Another aspect of the invention is safety threshold based distraction warnings. Warnings are provided that inform the driver of safety compromising distractive behavior. As appreciated hereinabove, drivers are often unaware of the effects of their distraction on their driving capabilities. Thus a goal of the safety based distraction warnings is to give the driver feedback about driving control task performance decrements. That is, if distraction is detected (i.e. glance behavior is over an appropriate safety threshold and/or vehicle performance deteriorates during glance behavior), the system provides one or more of the following alerts. A sound such as a simple beep or a performance-specific voice message referring to which performance decrements have been detected may be provided. For example, if glance behavior is above glance safety threshold standards (e.g. EU recommended 4 glances or 2 second single glance duration, US AAA recommended 10 second total glance duration), then the message "Visual Distraction Detected" or "Eyes off road extensively" can be issued. If steering is deviant during secondary task glance behavior, then the message "Inconsistent steering during visual distraction" can be issued. If lane keeping is deviant during secondary task glance behavior, then a message such as "Inconsistent lane-keeping during visual distraction" can be provided. If large_speed_ reduction is detected during secondary_task_glance_ behavior, then a message such as "Large speed reduction during visual distraction" can be issued. If multiple_causes are detected, then a generic message such as "Visual distraction detected" can be issued. If control task intrusion is detected during secondary task glance behavior, during different road types or different demand levels, then a corresponding warning is issued. The form(s) of the warnings can include a driver recorded or provided message, a seat vibration in a front part of seat or gaze redirection as described hereinbelow.

Figure 6:
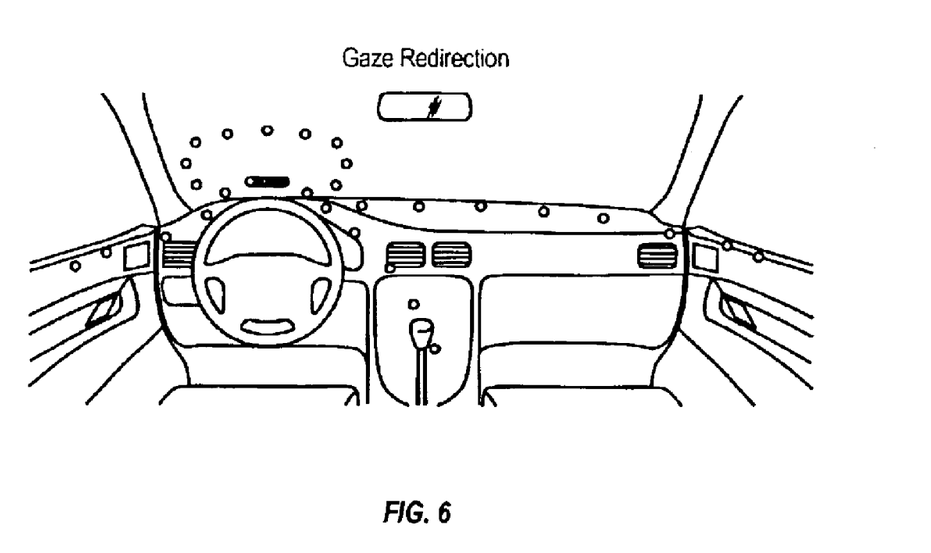
FIG. 6 depicts an exemplary embodiment for driver gaze redirection.

The present invention disclosure includes a new concept of "gaze redirection" that is illustrated in FIG. 6. Therein, an interface directs the driver' eyes to the forward driving scene (i.e.; through the front windshield) if driver distraction is detected. Exemplarily, a wave of light following one or more of the three LED "lines" (left, center, or right) will be initiated depending on where the drivers' gaze detected. After a wave of light, a large circle may optionally light up and then the central line of LEDs will light up; each purposed to more clearly focus the driver's attention where needed. The exact placement and timing of the several LED lights is not critical, nor is the color. In fact, the timing may be subliminal; that is, so fast that they are not consciously perceived. Alternatively, the appropriate lights may be first slowly flashed and the driver evaluated by the system to determine if corrective behavior has taken place. If not, the flash timing, as well as light intensity may be increased.

The set-up menu for distraction feedback may have exemplary logic as shown below:

| HMI Component | Option(s) |
| --- | --- |
| (1) Continuous distraction feedback | Continuous distraction feedback on/off |
| (2) Safety threshold based distraction warning | Voice message on/off<br>Performance specific message on/off<br>Default/multiple cause message on/off<br>User supplied message on/off<br>Seat vibration on/off<br>Gaze redirection on/off |

In another aspect, the present invention incorporates the concept of workload management with driving demand estimation derived from visual behavior of the driver. In general, the concept of a "workload manager" is a prioritization system that categorizes information and potentially delays presentation of the information to the driver until his or her workload is sufficiently low to avoid risk associated with the information's reception. The interfaces of integrated, in-vehicle information systems can be adapted to ensure that proper attention is being given to the driving task. The output from the distraction management algorithms referenced herein can be used as input to workload managers.

Workload managers of the type disclosed herein accurately measure driver workload using the driving demand visual activity measure of driving demand. Exemplarily, this is a non-bodily contact, on-board measure of how "visually active" a driver is; that is, head and eye movement (rotation) variability. This measure of head and eye movement is described in greater detail in U.S. Provisional Patent Application No. 60/418,171 filed 15 Oct. 2002, the disclosure of which is expressly incorporated herein by reference, including the "visual activity" algorithm described therein. Furthermore, the driving demand visual activity measure also enables new functionality in the Workload Manager HMI, disclosed herein.

One aspect of the workload manager is to pause dialogue of audible conversation or information. As examples, this includes system-initiated or auto-initiated information (e.g. text-to-speech email and non-critical navigation system information) and randomly-initiated spoken dialogue (e.g. incoming and outgoing telephone conversations) can be paused during periods of high visual activity.

As an example, a series of emails can be being delivered to the driver, for example, ten new emails from memory that are being "read" out loud by a text-to-speech system. During the course of such audio transmission, a period of high driver visual activity is detected by the management system. In response, the system pauses the audio transmission to avoid increasing the driver's attention load beyond pre-selected levels; such levels exemplarily corresponding to attention loads beyond which driving capabilities are compromised. Optionally, the management system can include an audible indication to the driver of such interruption via a tone or the like which may also serve as notice to the driver of the high attention load condition. The audible transmission can be resumed based on driver initiation or system initiation that is dependent on the system's detection of a sufficient reduction in attention load to a pre-selected level exemplarily corresponding to safe conditions for driver receipt of such audible information.

In another aspect, continuous and/or post-trip attention load feedback is enabled via the disclosed management system. This aspect has been enabled pursuant to the fundamental human behavior characteristic commonly referred to as the feedback principle; such principle generally holding that feedback enhances performance. This is true for both task/skill learning (e.g. learning to drive safely) and for job motivation. As appreciated hereinabove, drivers are typically poor judges of their own performance. The degree to which direct, accurate, immediate, and continuous information on task/skill performance is available is a key element in enhanced driver performance and motivation. Attention feedback constitutes a form of intrinsic driving feedback that has heretofore been otherwise unavailable to the driver. The approach is one of positive behavioral adaptation and lifestyle change rather than imminent collision warning. For example, some researchers believe that the main mechanism for increased alertness is "decision influence." The concept of decision influence stipulates that information of this nature (driver attention load and state-of-alertness) will influence a driver' decision about whether to stop for rest, drink coffee, reduce alcohol consumption or change other such behaviors.

An objective of attention feedback is thus to encourage positive behavior change over one or more of a plurality (multiple) of time-frames, for instance: (1) immediate (e.g. short-term compensatory behaviors like changing posture or aborting a complicated task); (2) trip (e.g. stopping for a nap, turning off mobile phone); (3) day-to-day (sleeping more after a low attention day, removing video screen from front seat); (4) and long-term (adoption of a different sleep lifestyle or distraction attitude). This feedback increases driver self-awareness of inattentive behavior and enables better self-management.

Two main feedback types are considered. The first is continuous in-vehicle feedback that provides the driver with real-time attentive performance information, for example information presented while driving. This information is communicated in a way that, in itself, does not jeopardize safety. The concept is to provide a sort of attention-meter, alertness meter (alert-o-meter), or safe/unsafe driving performance meter. The second feedback type is post-trip feedback that provides the driver with more detailed attentive performance information once driving has stopped.

Saving post-trip feedback "to file" further allows fleet-based safety feedback to focus on source behaviors as opposed to outcome measures such as accident incidents. One option, perhaps contributing to driver acceptance, is the provision of a tiered system. In such a tiered system, drivers have continuous access to data, fleet managers have access to summarized data, and regulating agencies can be granted access to summary data. Therefore, in the instance of fleet drivers, the invention can be better enjoyed as a helpful tool, without necessarily having to induce driver apprehension about employer-reporting characteristics.

Figure 7:
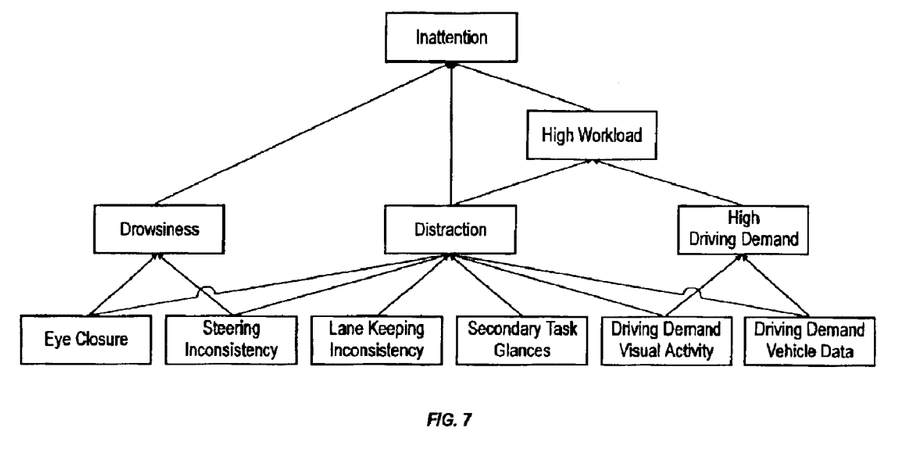
FIG. 7 diagrammatically illustrates interaction of constituent components of driver inattentiveness.

To be able to give attention feedback, the management system has to be operationalized. Inattention may be seen as being comprised of drowsiness/impairment, distraction, and high workload factors. Therefore, and as illustrated in FIG. 7, an integrated model considering each type of inattentiveness is preferred. Therein, one system model configured according to the present invention is shown that can selectively consider driver inattention, workload, and personal characteristics such as drowsiness and distraction.

Figure 8A:
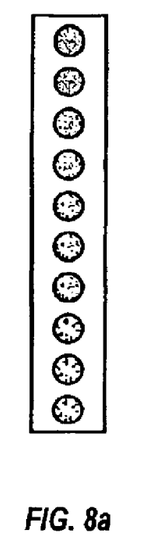
FIGS. 8(a)–(c) illustrate various "active" graphical displays for displaying real-time driver information according to the teachings of the present invention.
Figure 8B:
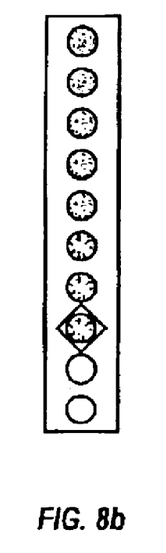
Figure 8C:
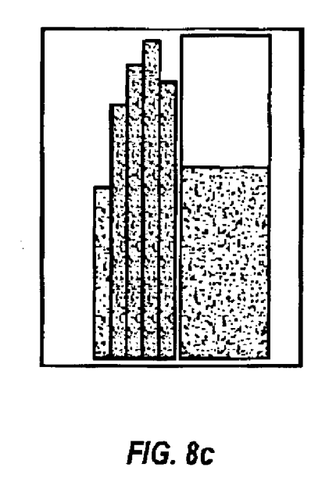

In another aspect of the present invention, unique ways are provided for displaying various information or feedback to the driver. In the instance of continuous attention-feedback, FIGS. 8(a)–(c) demonstrate various "active" graphical displays for displaying real-time driver information that has been sensed or generated by the management system. As an example, the display can be of a "generic" or synthesized attention feedback quantity such as the level of attention/inattention as a combined measure of drowsiness, distraction, and workload. In the instance of FIG. 8(a), a simple stack of lights with no trend information is exemplified. In the instance of FIG. 8(b), an "aircraft radar type" display is utilized in which a box is positioned around the current level and trend information in the form of "fading out" is enabled. FIG. 8(c) demonstrates a histogram in which instantaneous "real time" information is shown as an elongating/retracting bar (relatively wide) on the right, with aggregate statistical values (average, median, and the like) for periods of pre-selected duration represented by the more narrow bars on the left. In this manner, trend information is demonstrated. In the illustrative example of FIG. 8(c), five previous periods are represented. It should be appreciated that any previous periods may be displayed according to the control logic for the display and memory capacity.

Figure 9:
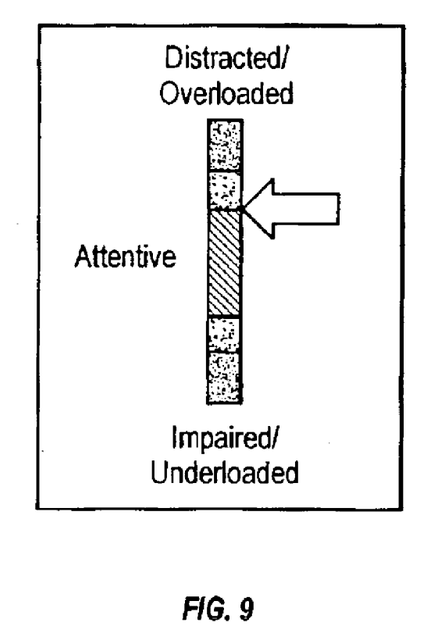
FIG. 9 provides an illustration of real-time driver feedback in a comparative format against an indication of an optimal level of attention.

In another aspect, the present invention also provides real-time driver feedback in a comparative format against an indication of an optimal level of attention. An exemplary embodiment of such a display is illustrated in FIG. 9 where a driver may observe his or her degree of distraction or overload relative to optimum attentiveness.

Figure 10:
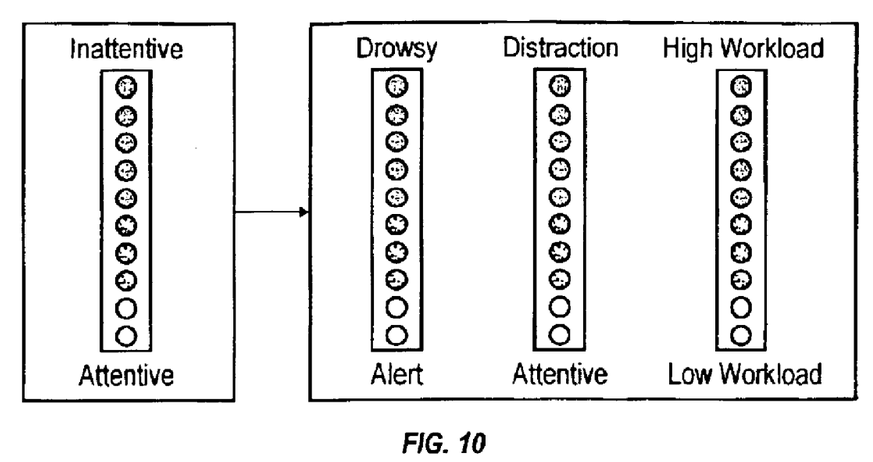
FIG. 10 provides an illustration of an exemplarily formatted explanation of the basis for the detected increased workload/inattention level.

In still another aspect, the invention may be used to measure detected periods of driver inattention, with notification of the state provided. The driver may then "ask" (e.g. by touching a screen, for instance) what the problem was and receive an explanation of the basis for the detected increased workload/inattention level. Such feedback can exemplarily be provided in the form of verbal messages and/or graphically as shown in FIG. 10. Therein, three graphic representations of drowsiness, distraction, and workload are depicted on the right, and a combination of the effects is demonstrated on the left where relative driver attentiveness is indicated.

Figure 11:
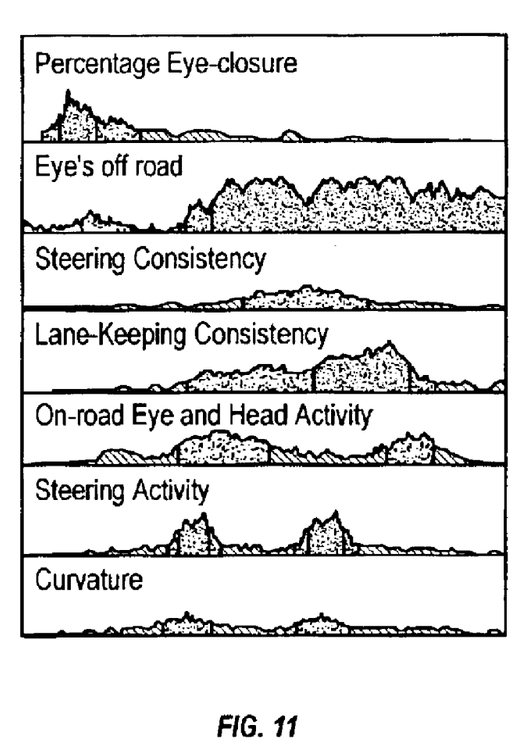
FIG. 11 provides an exemplary illustration of on-screen post-trip feedback.

As explained above, the aspect of trip-reporting can be highly advantageous for the driver' learning and behavior modification. Therefore, inventive ways to provide on-screen post-trip feedback are disclosed and exemplarily illustrated in FIG. 11. In this illustrative example, a menu choice from a display screen has been selected for post-trip feedback and the associated display of such measured characteristics as percent eye-closure, steering consistency and the like have been displayed in a historical format. Of course, this same information can advantageously be logged for later analysis and use.

The driver capabilities that have been discussed above can also be utilized for distraction adaptation of other vehicle systems such as forward-collision, rear-collision and lane-change collision warning (FCW, RCW and LCW) systems. Rear-end collisions account for approximately twenty-eight percent of automotive crashes. Because driver inattention is a contributing factor in more than sixty percent of these collisions, collision warning and avoidance systems are important tools for reducing crashes and saving lives. One objective of the present attention management systems is to detect the co-occurrence of inattention and safety critical events in the traffic environment; for example, sudden braking of a lead vehicle and driver eyes-off-road conditions. Two examples of this can be used as visual behavior information to adapt forward collision—and lane change—warnings.

Integration of detection of quantified secondary tasks (e.g. by detecting button presses or eye movements) greatly enhances the collision warning system by dynamically adjusting the collision warning threshold according to whether the driver is engaged with a potentially distracting device or other type task. For example, the collision warning system could generate a warning earlier if it is detected that the driver is involved in a cellular telephone conversation. An early collision warning helps the driver react more quickly and avoid more collisions compared to late warning, or no warning at all. If the driver is inattentive with respect to a certain aspect of the driving task, for example looking away from forward when a likelihood of forward collision is detected, or has not looked sideways when a possible lane change collision is detected, then warnings of such conditions are initiated earlier. Studies have shown that even a one second earlier warning when drivers are looking away is highly effective for avoiding collisions.

If it is detected that the driver is attentive, then the warnings can be delayed or even cancelled. A delay in warning presentation allows more time for the forward collision and lane change warning algorithms to more certainly ascertain that a warning is needed, thereby reducing false alarms. Still further, driver cancellation wherein the driver chooses not to have collision warnings active when looking at the road or side mirrors would also eliminate annoying false alarms.

Figure 12:
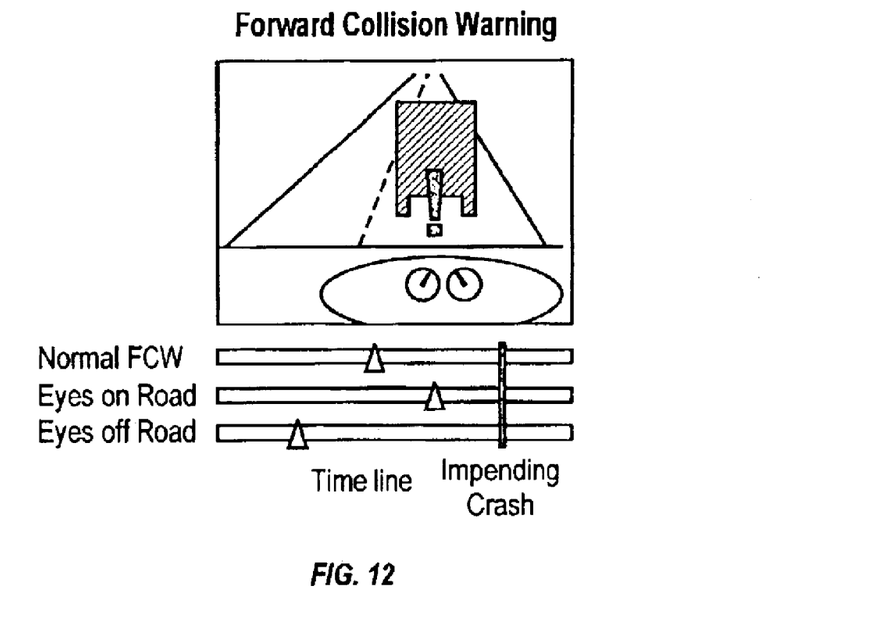
FIG. 12 provides an exemplary illustration of a heads-up or screen display warning for forward collision situations.
Figure 13:
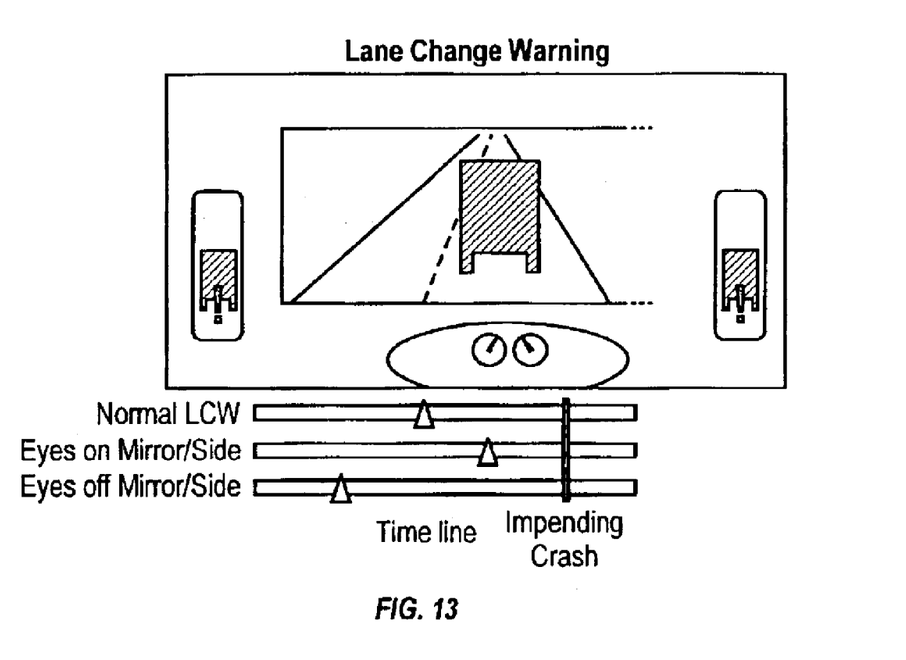
FIG. 13 provides an exemplary illustration of a heads-up or screen display warning regarding lane-change collision situations.
Figure 14:
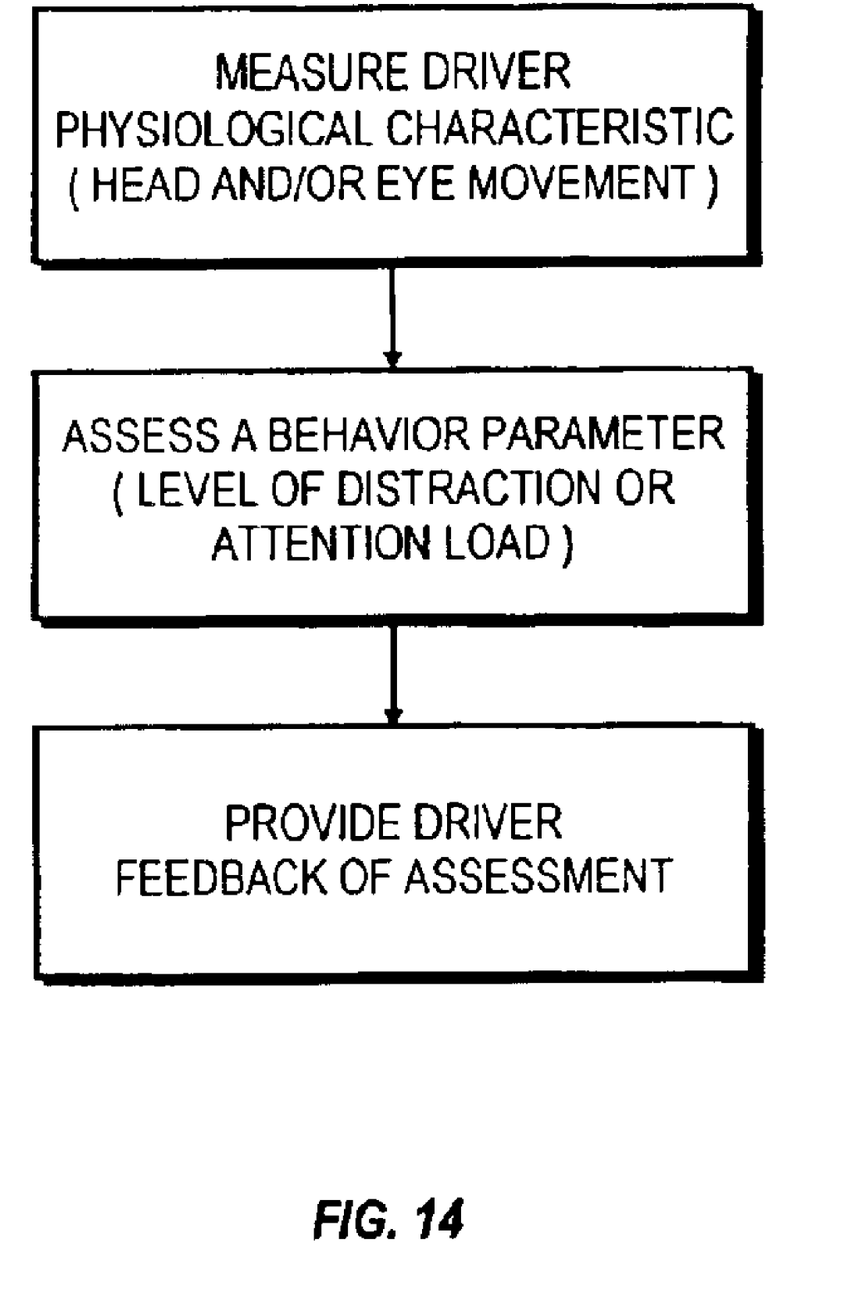
FIG. 14 provides an exemplary flow chart for a system and method conducted according to the present invention in which a measure is made of a driver physiological characteristic such as head and/or eye movement. In another step, a behavior parameter is assessed such as level of driver distraction or attention load. In still another step, feedback regarding the assessment is made to the driver.

As an implementation strategy, in a first stage, such warnings may be "soft," but increasing in intensity as conditions worsen and a crash becomes more imminent. In the instance of forward collision warning, a heads-up or screen display warning may first be called up, but later being joined by an audible warning sounded as crash conditions intensify. An example of such a warning and its control parameters (which may or may not be displayed to the driver) are depicted in FIG. 12 regarding forward collision situations and FIG. 13 regarding lane-change collision situations.

The detection features described hereinabove with regard to driver characteristics may be utilized in other environments and for other purposes than expressly described. The detection features may also be integrated for employment in other in-vehicle systems. For instance, as a passive safety feature, a "smart" airbag may be enabled that detects when the driver'/passenger' head is not in a proper position to receive a deployed airbag. Responsively, deployment of the airbag may be modified to accommodate the sensed head position.

In another capacity, sensed behavior could be used to identify the driver, or at least rule out that an authorized driver is behind the wheel thereby facilitating theft protection. The head and eye sensors could also be used to automatically configure mirrors, seat positions and the like. Mouth tracking can be used to enhance speech recognition accessories. Filters for oncoming headlights can be adapted, as can displays for the driver based on eye position and motion.

What is claimed is:

1. A method for assessing a driver's excessive distraction from driving control tasks due to the driver's performance of secondary tasks and responsively stimulating the driver's attention to the driving control tasks, said method comprising:

taking a series of non-bodily contact, on-board measurements of a driver's head or eye movement and inputting the measurements to a computer processor for analysis;

analyzing the input measurements using the computer processor and determining therefrom whether an excessive amount of driver attention is being paid to a secondary task based on an assessment of driver workload; and initiating stimulation of the driver's attention to driving control tasks when excessive driver attention to a secondary task is assessed.

2. The method as recited in claim 1, further comprising: detecting a driving control task performance decrement prior to stimulating the driver's attention to driving control tasks.

3. The method as recited in claim 2, wherein said driving control task performance decrement is assessed based on inconsistent steering.

4. The method as recited in claim 2, wherein said driving control task performance decrement is assessed based on inconsistent lane keeping.

5. The method as recited in claim 2, wherein said driving control task performance decrement is assessed based on inconsistent vehicle speed.

6. The method as recited in claim 1, further comprising measuring the driver's head movement in the assessment of driver workload.

7. The method as recited in claim 1, further comprising said driver's eye movement being rotational movement of the eye.

8. The method as recited in claim 1, further comprising analyzing the driver's glance behavior for the assessment of driver workload.

9. The method is recited in claim 1, further comprising: comprising assessed level of driver workload to a predetermined acceptable level and visually presenting results of the comparison to the driver.

10. The method as recited in claim 1, further comprising: utilizing an audible driver alertness stimulation mode to stimulate the driver's attention to driving control tasks.

11. The method as recited in claim 10, wherein said audible driver alertness stimulation mode is a user-recorded message.

12. The method as recited in claim 1, further comprising: utilizing a tactile driver alertness stimulation mode to stimulate the driver's attention to driving control tasks.

13. The method as recited in claim 12, wherein said tactile driver alertness simulation mode is seat vibration.

14. The method as recited in claim 1, further comprising: utilizing one of a plurality of selectable driver alertness stimulation modes to stimulate the driver's attention to driving control tasks.

15. The method as recited in claim 14, further comprising selecting a particular driver alertness stimulation mode from the plurality of selectable driver alertness stimulation modes based on existing driver visual activity.

16. The method as recited in claim 14, further comprising enabling driver selection of the particular driver alertness stimulation mode to be utilized from the plurality of selectable driver alertness stimulation modes.

17. The method as recited in claim 16, further comprising enabling driver selection of up to three driver alertness stimulation modes from the plurality of selectable driver alertness stimulation modes.

18. The method as recited in claim 17, further comprising:
simultaneously activating up to three driver alertness stimulation modes selected by the driver when high workload is assessed.

19. The method as recited in claim 1, further comprising adapting a driver alertness stimulation mode utilized to stimulate the driver's attention to driving control tasks based on existing driver visual activity.

20. The method as recited in claim 1, further comprising redirecting the driver's visual attention in a different direction.

21. The method as recited in claim 20, wherein the different direction to which the driver's visual attention is redirected is to the forward driving scene.

22. The method as recited in claim 20, wherein the redirection of the driver's visual attention is affected by a wave of light.

23. The method as recited in claim 22, wherein the wave of light is subliminal to the driver.

24. The method as recited in claim 22, wherein the wave of light is constituted by a progressive illumination of a series of lights.

25. The method as recited in claim 22, wherein the wave of light initiates from a location approximately corresponding to a detected position of the driver's gaze.

26. The method as recited in claim 22, wherein the wave of light terminates in a light area greater than the width of the light path of the light.

27. The method as recited in claim 22, wherein the wave of light first slowly flashes thereby permitting evaluation of the driver's reaction.

28. The method as recited in claim 27, further comprising increasing a flash time of the wave of lights upon insufficient driver reaction being detected.

29. The method as recited in claim 27, further comprising increasing an intensity of the wave of lights upon insufficient driver reaction being detected.

30. The method as recited in claim 1, further comprising warning the driver and informing the driver of an assessed cause of the warning.

31. The method as recited in claim 30, wherein the assessed cause of the warning is inconsistent steering.

32. The method as recited in claim 31, wherein a visual depiction of inconsistent steering is displayed to the driver.

33. The method as recited in claim 31, wherein an audible message informing the driver that inconsistent steering is occurring is played to the driver.

34. The method as recited in claim 30, wherein the assessed cause of the warning is inconsistent lane keeping.

35. The method as recited in claim 34, wherein a visual depiction of inconsistent lane keeping is displayed to the driver.

36. The method as recited in claim 34, wherein an audible message informing the driver that inconsistent lane keeping is occurring is played to the driver.

37. The method as recited in claim 1, further comprising:
determining, based on existing visual activity, a probable source of an assessed high level of driver workload, and based thereupon, selecting a particular driver alertness stimulation mode from a plurality of possible stimulation modes.

38. The method as recited in claim 37, wherein said existing visual activity indicative of high workload is characterized by excessively frequent glancing toward substantially the same location.

39. The method as recited in claim 1, further comprising:
implementing workload management protocols based on an assessment of high workload.

40. The method as recited in claim 39, wherein said workload management protocols comprise a prioritization system that categorizes information and delays presentation of the information to the driver when high workload is assessed.

41. The method as recited in claim 40, wherein the information delayed to the driver is audible speech from an electronic device.

42. The method as recited in claim 41, wherein the audible speech is conversation emitting from an onboard telephone.

43. The method as recited in claim 41, wherein the audible speech is position information emitting from an onboard navigation system.

44. The method as recited in claim 41, wherein the audible speech is navigational instruction emitting from an onboard navigation system.

45. The method as recited in claim 41, wherein the audible speech is text-to-speech electronic translation.

46. The method as recited in claim 41, wherein the audible speech is text-to-speech electronic translation of email messages.

47. The method as recited in claim 40, further comprising:
resuming information delivery when acceptable driver characteristics resume.

48. The method as recited in claim 1, further comprising:
assessing an acceptable level of driver attentiveness to driving controls tasks, and based thereupon, delaying stimulation of the driver's attention to driving control tasks.

49. The method as recited in claim 1, further comprising:
assessing an acceptable level of driver attentiveness to driving control tasks, and based thereupon, canceling stimulation of the driver's attention to driving control tasks.

50. The method as recited in claim 1, further comprising:
classifying a specifically characterized driver visual activity as being related to the performance of driving control tasks that would otherwise be assessed as an unacceptable driver visual activity and preventing stimulation of the driver.

51. The method as recited in claim 50, wherein said driver visual activity is glancing toward rearview mirrors.

52. The method as recited in claim 1, further comprising:
adapting the performance of a forward-collision warning system.

53. The method as recited in claim 1, further comprising:
adapting the performance of a rear-collision warning system.

54. The method as recited in claim 1, further comprising:
adapting the performance of a lane-change-collision warning system.

55. The method as recited in claim 1, further comprising:
providing driver feedback in the form of a real-time representation of assessed driver workload.

56. The method as recited in claim 55, wherein said driver feedback is provided in the form of a light stack in which the number of illuminated lights in the stack correlates to an assessed level of driver workload.

57. The method as recited in claim 55, wherein said driver feedback is provided in the form of a light stack upon which an assessed level of driver workload is indicated along a length thereof.

58. The method as recited in claim 57, wherein trend information pertaining to recent assessed levels of driver workload are indicated in fade-out.

59. The method as recited in claim 55, wherein said driver feedback is provided in the form of an extending and retracting light bar, the illuminated length of which correlates to a real-time assessed workload.

60. The method as recited in claim 59, further comprising adjacently located, fixed length light bars, each demonstrating a historical statistical value of assessed workload.

61. The method as recited in claim 60, wherein said adjacently located, fixed length light bars have a more narrow width than said extending and retracting light bar.

62. The method as recited in claim 55, wherein said driver feedback is provided in a comparative format showing real-time assessed workload level relative to an optimum workload level.

63. The method as recited in claim 55, wherein said driver feedback is provided in the form of a histogram of assessed workload.

64. The method as recited in claim 1, further comprising:
logging said assessed workload and providing driver feedback in the form of a post-trip report.

65. The method as recited in claim 1, further comprising:
determining a probable source of a driver's assessed high workload, and identifying said probable source to said driver upon demand.

* * * * *